US009687220B2

(12) United States Patent
Tobias

(10) Patent No.: US 9,687,220 B2
(45) Date of Patent: Jun. 27, 2017

(54) DEVICE FOR SECURING AN OBJECT TO A SUBJECT AND WOUND CLOSURE

(71) Applicant: University of Tennessee Research Foundation, Knoxville, TN (US)

(72) Inventor: Karen M. Tobias, Knoxville, TN (US)

(73) Assignee: UNIVERSITY OF TENNESSEE RESEARCH FOUNDATION, Knoxville, TN (US)

(*) Notice: Subject to any disclaimer, the term of this patent is extended or adjusted under 35 U.S.C. 154(b) by 753 days.

(21) Appl. No.: 14/032,024

(22) Filed: Sep. 19, 2013

(65) Prior Publication Data

US 2014/0088620 A1   Mar. 27, 2014

Related U.S. Application Data

(60) Provisional application No. 61/704,221, filed on Sep. 21, 2012.

(51) Int. Cl.
*A61B 17/08* (2006.01)
*A61B 17/04* (2006.01)

(52) U.S. Cl.
CPC ........ *A61B 17/0401* (2013.01); *A61B 17/083* (2013.01); *A61B 2017/088* (2013.01)

(58) Field of Classification Search
CPC ........ A61B 17/0401; A61B 2017/0403; A61B 2017/0404; A61B 2017/0406;
(Continued)

(56) References Cited

U.S. PATENT DOCUMENTS 1,766,532 A * 6/1930 Pflueger ................ A01K 91/03
    43/43.1
4,901,721 A * 2/1990 Hakki .............. A61B 17/06166
    24/27

(Continued)

OTHER PUBLICATIONS

Adams et al., "The crouton dressing: an alternative technique to immobilize skin grafts in difficult areas", Burns. Mar. 2012;38(2):301-3. doi: 10.1016/j.burns.2011.09.016. Epub Oct. 24, 2011.
Wheeless, Jr., Skin-Stretching System Versus Skin Grafting Atlas of Pelvic Surgery, On-Line Edition, http://www.atlasofpelvicsurgery.com/10MalignantDisease/24Skin-StretchingSystemVersusSkinGraft/cha10sec24.html; Mar. 30, 2009.
(Continued)

*Primary Examiner* — Tuan V Nguyen
*Assistant Examiner* — Chima Igboko
(74) *Attorney, Agent, or Firm* — FisherBroyles, LLP; Jason M. Pass

(57) ABSTRACT

Disclosed are devices, methods, and systems for securing an object to a subject, such as bandages and dressings over wounds, keeping wounds apposed, maintaining pressure on wounds, and stretching skin. The device comprises a closeable, needle-tipped anchor; a lacing loop; and, a swivel connector that connects the anchor and lacing loop and permits rotation and sliding of the connecting parts. The needle tipped anchor is inserted through the tissues, and its tip is then locked in position with the clasp. Multiple devices may be placed around the wound along its edges. Lacing material is engaged in the lacing loop by passage of the lacing material through the lacing loop. The swivel permits rotation and also permits sliding at its connections with the anchor and lacing loop. This range of motion allows positioning and tightening of the laces without inappropriate torque on tissue to which the anchor is attached.

20 Claims, 9 Drawing Sheets

(58) Field of Classification Search
CPC .... A61B 2017/0408; A61B 2017/0417; A61B 2017/0419; A61B 2017/0422; A61B 2017/0425; A61B 2017/0433; A61B 2017/0445; A61B 2017/0446; A61B 2017/0448; A61B 2017/045; A61B 2017/0451; A61B 2017/0456; A61B 2017/0459; A61B 2017/0458; A61B 2017/088; A61B 17/083

USPC ........ 606/232, 216, 217, 218; 119/769, 770, 119/792, 795

See application file for complete search history.

(56) References Cited

U.S. PATENT DOCUMENTS

| | | | |
|---|---|---|---|
| 5,234,462 | A | 8/1993 | Pavletic |
| 7,455,681 | B2 | 11/2008 | Wilke et al. |
| 7,686,829 | B2 | 3/2010 | Elliott et al. |
| 7,927,352 | B2 | 4/2011 | Wilke et al. |
| 7,927,362 | B2 | 4/2011 | Shippy, III et al. |
| 8,864,796 | B2 | 10/2014 | Elliott et al. |
| 2005/0241213 | A1* | 11/2005 | Garber ............ A01K 91/03 43/21.2 |
| 2008/0269786 | A1* | 10/2008 | Nobles ............ A61B 17/0057 606/145 |
| 2009/0282725 | A1* | 11/2009 | Kuhlman ............ A01K 83/00 43/34 |
| 2012/0245632 | A1* | 9/2012 | Tsai ............ A61B 17/0401 606/232 |
| 2013/0035720 | A1* | 2/2013 | Perriello ............ A61B 17/0401 606/232 |
| 2013/0133240 | A1* | 5/2013 | Beitzel ............ A01K 83/00 43/43.16 |

OTHER PUBLICATIONS

Barnea et al., "Delayed primary closure of fasciotomy wounds with Wisebands, a skin- and soft tissue-stretch device".

Bostrom et al., "The Use of an External Skin-Stretching Device for Wound Management in a Rabbit (*Oryctolagus cuniculus*)" Journal of Exotic Pet Medicine. 2006, 15(2):145-149.

Cheng et al., "Experience with elastic rubber bands for the tie-over dressing in skin graft", Burns. Mar. 2006;32(2):212-5. Epub Jan. 31, 2006.

Coban, "A novel tie-over technique for skin graft fixation of circular defects: star tie-over", Burns. Sep. 2007;33(6):801-2. Epub Jul. 6, 2007.

Gado et al., "Skin grafting: comparative evaluation of two dressing techniques in selected body areas", In Vivo. Jul.-Aug. 2008;22(4):503-8.

Kanjoor et al., "Role of Skin Stretching Device for Wound Closure", Eur. J. Plast. Surg., 2002, 25:323-326.

Kim et al., "The tie-over dressing using skin-staples and round rubber bands", Br J Plast Surg. Jul. 2005;58(5):751-2.

Medina et al., "The use of an innovative device for wound closure after upper extremity fasciotomy", Hand (N Y). Jun. 2008;3(2):146-51. doi: 10.1007/s11552-007-9082-y. Epub Dec. 1, 2007.

Taylor et al., "Early results using a dynamic method for delayed primary closure of fasciotomy wounds", J Am Coll Surg. Nov. 2003;197(5):872-8.

Topaz, et al., "The TopClosure® 3S System, for skin stretching and a secure wound closure", Eur J Plast Surg. Jul. 2012;35(7):533-543. Epub Jan. 18, 2012.

"Instructions for Use: DermaClose. Continuous External Tissue Expander". Chanhassen, MN: wct inc., 2014, print (2 pages).

"Using DermaClose with Negative Pressure Wound Therapy (NPWT)", Chanhasse, MN: wct inc., 2014, print (2 pages).

"Six Anchor Technique" Chanhasse, MN: wct inc., 2014, print (2 pages).

* cited by examiner

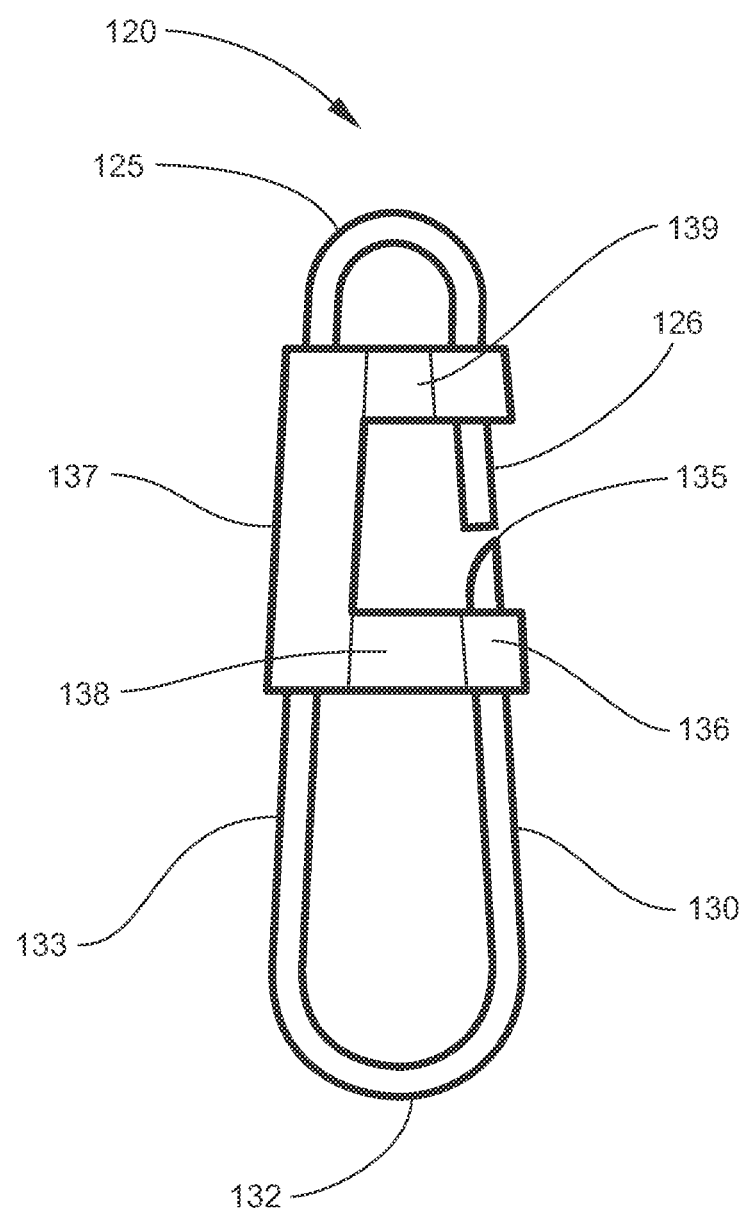

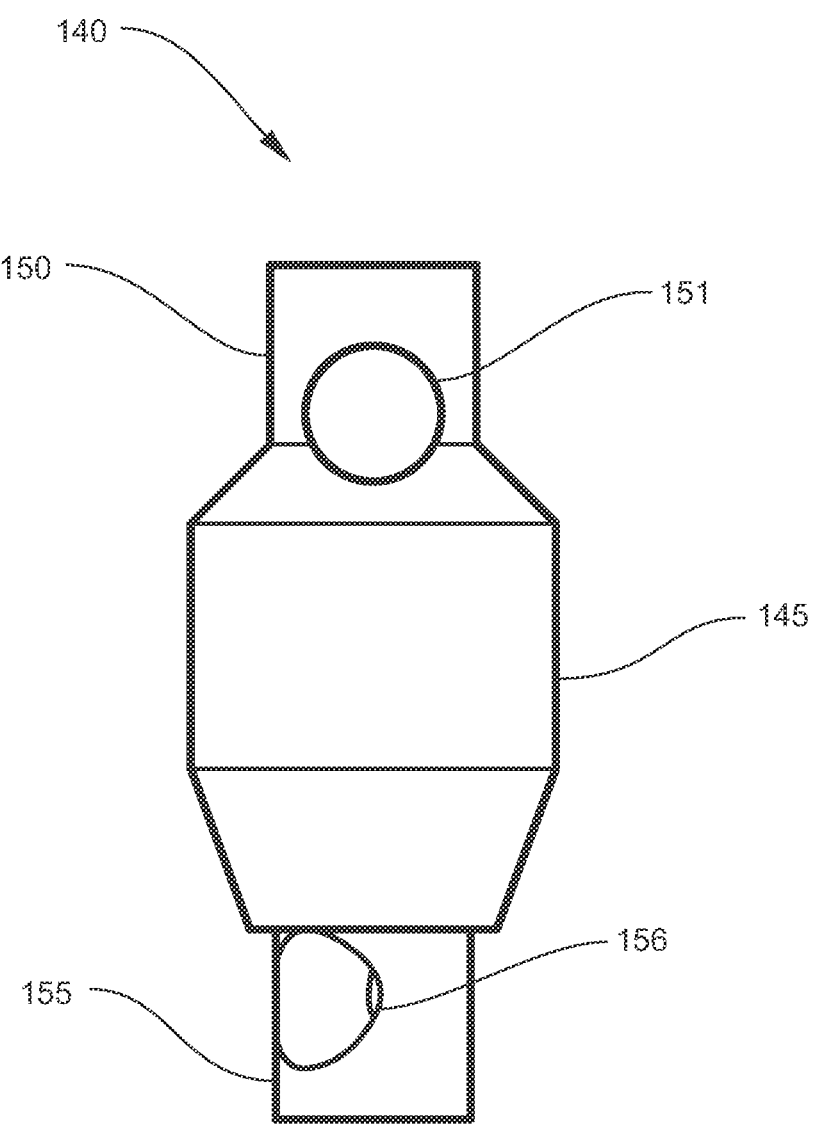

DEVICE FOR SECURING AN OBJECT TO A SUBJECT AND WOUND CLOSURE

CROSS-REFERENCE TO RELATED APPLICATION

This application claims the priority benefit of U.S. Provisional Application 61/704,221 filed on Sep. 21, 2012, which is incorporated by reference herein in its entirety.

FIELD OF THE DISCLOSURE

This disclosure relates generally to medical equipment and, more particularly, to devices, systems, and methods for securing an object to the tissue of a subject.

BACKGROUND

Tissue damage, such as tissue separations, lacerations, open wounds, and punctures, arise from a variety of causes. Tissue separation may result from surgical procedures, for example, whereas open wounds may result from traumatic injury. Further, different types of wounds often require unique types of treatment depending on the progression of wound healing. For example, the goal with acute tissue damage treatment may be to control bleeding, whereas long term wound care may be aimed at reducing scarring, eliminating the potential of hematoma, seroma, and "dead-space" formation, as well as managing pain.

A variety of dressings and bandages, along with numerous techniques for applying dressings and bandages, are used to treat tissue damage. One technique for treating open wounds is the tie-over technique. In animals, for example, the tie-over technique involves placement of multiple suture loops in the skin around a wound. A bite of skin is taken with the suture needle. The suture is tied in a knot near the skin. A loop is formed above the knot, and two more knots are tied to maintain the loop's size and shape. With a traditional tie-over bandage, lacing material is threaded through the suture loops in a crisscross fashion, tightened over a bandage or dressing, and tied in place. The lacing material is cut when the bandage is to be changed, and the suture loops are reused for subsequent bandage or dressing placement.

In humans, skin sutures are placed to secure skin grafts over a wound and are used to hold a tie-over bandage. Essentially, the stitches are placed between the graft and the skin edge on each side of the graft and are left long and tied together over a bandage. This means that the sutures are constantly being pulled where the skin and graft are trying to heal together, thus inhibiting healing. Also, the sutures may be difficult to reuse when needed, i.e., for reuse they must be tied in a bow or some other fashion over the top of the dressing and then untied to change the dressing. This is challenging, particularly with normal sized skin sutures.

Placement of the suture loops is time consuming and usually requires anesthesia. Formation of the suture loops can also be challenging because the suture used to make the loops is usually stiff and does not hold knots well. If the knots slip, the loops shrink and loops disappear, eliminating their usefulness for lace placement. If more pliable suture is used to make the loops, the loops flatten out, making lace placement difficult. Tie-over bandages also inhibit freedom of motion, thus causing patient non-compliance. A dog, for example, may scratch or pull at a bandage that is overly limiting and irritating or may get increased limb swelling from lack of motion.

Previous studies have shown that application of tension with a tie-over bandage recruits up to 30% more skin within a 72 hour period. Yet suture loops may not tolerate the amounts of tension needed and can break or stretch out. Systems for skin stretching have been developed from adhesive anchors that secure to elastic tape by hook-and-loop-type connections (such as Velcro) or to lacing materials by incorporated hooks. In dogs and cats, hair growth, desquamation, and skin oils interfere with adhesion of these anchors, and super glue may need to be applied to keep them attached. Removal of the adhesive anchors can cause trauma to the underlying skin. Also, the amount of tension that can be applied to the skin is limited by how well and how long the anchor pads stick and how well the elastic band-anchor connection or lacing-anchor connection can resist the upward and outward forces of the underlying dressing and any patient motion. Other designs (e.g., Sure Close, Wise Band, Silver Bullet, S.T.A.R. Device, Dermaclose) are bulky, do not incorporate bandages, or are not meant for irregularly shaped wounds, thick skin, or active patients.

A need thus exists for devices, systems, and methods for treating tissue damage that solves these and other problems associated with securing objects, such as bandages and other medical devices, to a subject's tissue. More particularly, a need exists for devices, systems, and methods that facilitate the convenient and rapid closure of wounds and that allow rapid placement of bandages, such as tie-over bandages, during wound treatment. A need also exists for providing a secure anchor to a subject's tissue that is independent of tissue thickness or type or presence of hair, oils, or moisture. A need also exists for an easy and convenient means for securing objects to the tissue of a subject, such as the skin, that does not require sutures.

SUMMARY OF THE DISCLOSURE

This disclosure addresses the above needs and others. More particularly, disclosed are alternative and improved devices, systems, and methods for attaching an object to a subject. Further disclosed are alternative and improved devices, systems, and methods for wound or tissue closure. In certain embodiments, disclosed is a device for attaching an object to a subject, comprising an anchor, a swivel connector, and a lacing loop.

Also disclosed is a system for attaching an object to a subject. The system comprises two or more devices that comprise an anchor, a swivel connector, and a cord loop. In some embodiments, the device comprises only the anchor or anchor and swivel. The system further comprises a lacing material, wherein the lacing material is threaded through the two or more devices. Also disclosed are methods for using such a system. In some embodiments, the length of the lacing material is predetermined. In some embodiments, the lacing material is adjustable.

Further disclosed are methods for treating wounds and for wound closure using the devices and systems disclosed herein. For example, disclosed is a method for securing an object to a subject, comprising attaching an anchor to the tissue of a subject, wherein the anchor comprises a needle tip, a needle shaft, a needle arc, a support shaft, a connector arc, and an enclosure arm; threading a lacing material through a lacing loop, wherein the lacing loop is operably connected to the anchor; and, affixing the object to the subject with the lacing material.

The devices, systems, and methods disclosed herein may also be used to impart tension on skin and other tissues, for example, in order to assist in wound closure. They may also be used to recruit tissue, such as increasing the amount of available skin, before the closure of a wound. The devices and methods disclosed herein may also be used to and to place pressure on wounds in order to reduce hemorrhage or development of fluid pockets, for example.

The foregoing and other features and advantages of the disclosure will become more apparent from the following detailed description, which proceeds with reference to the accompanying figures.

BRIEF DESCRIPTION OF THE DRAWINGS

FIG. 2 is a front perspective view of an exemplary embodiment of an anchor of the device for securing an object to a subject.

FIG. 4 is a side perspective view of an exemplary embodiment of a swivel connector of the device for securing an object to a subject.

DETAILED DESCRIPTION

I. Summary of Terms

Figure 1:
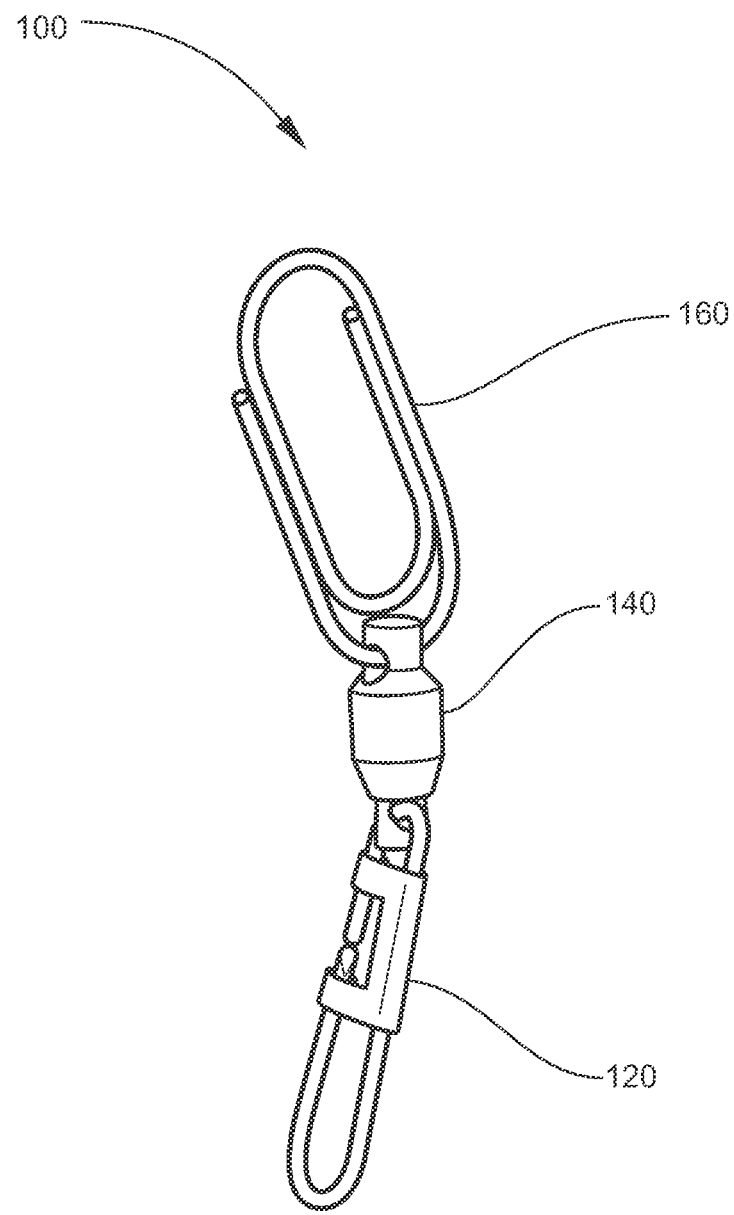
FIG. 1 is a perspective view of an exemplary embodiment of a device for securing an object to a subject.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value.

As used herein, "fastener" refers to any means for fastening or connecting one or more items together. Such fasteners include, for example, clasps, clamps, clips, hooks, buckles, hook-and-loop materials (such as Velcro), straps, ropes, carabiners, tapes, string, wire, suture, cable ties, laces, umbilical tape, rubber bands, elastic bands, bungee cord, or sewing elastic.

As used herein, the term "object" refers to any device, such as a medical device, that may be attached or secured to a subject. Objects include, for example, tubes, elimination tubes, chest tubes, drains, hoses, catheters, medication or insecticidal delivery systems, information tags, identification, suction units, pumps, medication delivery pumps, suction devices, monitors, infusion catheters, urinary catheters, drainage catheters, venous catheters, arterial catheters, central line and peripheral line catheters, suction drains, cannulas, wound packings, dressings, gauze, gauze packing, wound drains, nasal oxygen tubes, nasoesohageal or nasogastric tubes, gastroenteric feed tubes, and endotracheal tubes, restraint devices, collars, Elizabethan collars, bandages, short and long stretch bandages, triangular bandages, tube bandages, compression bandages, roller bandages, strap bandages, suspensory bandages, four-tailed bandages, elastic and non-elastic bandages, stockinette bandages, tie-over bandages, rubberized or plastic coverings, cloth coverings, neoprene coverings, nylon coverings, protective devices or coverings, research equipment, noise-emitting devices, light delivering devices, light sensing devices, or motion sensing devices.

As used herein, "wound" or "wounds" refers to tissue damage or tissue loss of any kind, including, for example, open wounds, closed wounds, penetrating wounds, and skin abnormalities. Such "wounds" include incisions (including surgical incisions), abrasions, lacerations, cuts, sores, contusions, burns, amputations, skin tears, bullet wounds, stab wounds, crushing injuries, punctures, perforations, fistulae, sinuses, exposed implants, exposed bond, degloving injury, avulsion, shearing wounds, fungal wounds, immune mediated wounds, mycobacterial wounds, paraneoplastic wounds, panniculitis, granulomas, lesions, eroding ulcers, ulcers such as diabetic foot ulcers, lower leg ulcers, pressure ulcers, wounds caused by infection such as Gangrene, radiation burns, post-operative non-infected and infected wounds, slow or non-healing surgical wounds, wounds from bites such as from snakes or insects or animals, skin/muscle grafts or flaps including failing or compromised skin/muscle grafts or flaps, inflamed or traumatized areas of skin, a draining or bleeding sites, a tumor, exposed abdominal wall, exposed muscle, exposed thoracic wall, exposed bone, exposed subcutaneous tissue, abscesses, or excoriation.

As used herein, the term "tissue" refers to generally refers to any type of biological tissue of a subject and includes connective, muscle, nervous, and epithelial tissues. As would be appreciated by one skilled in the art, "tissue" includes individual or groups of cells of a bodily tissue. The "tissue" may also be a whole organ or any portion of a bodily organ. Connective tissue, for example, supports organs, fills the spaces between organs, and forms tendons, ligaments, and cartilage. Epithelial tissue, such as that comprising the skin, for example, is generally present in a single layer of cells held together via occluding junctions to create a selectively permeable barrier. Tissue of the skin, for example, generally includes an epidermis layer, a dermis layer, and a subcutaneous layer.

As used herein, the term "lacing material" refers to any material that can be threaded through an opening or fastened to an opening, for example. As those skilled in the art will appreciate, such materials include rope, string, shoe lace, boot lace, thread, filament, fishing line, umbilical tape, belts, nylon, cord, cable, webbing, bungee cords, suture, elastic bands or elastic material, sewing elastic, wire, rubber bands and rubber banding materials, tie, cable ties, straps, and wire. Such lacing material, for example, may be elastic/non-elastic or resilient/non-resilient.

As used herein, the term "subject" refers to a living, multicellular vertebrate organism, a category that includes, for example, mammals and non-mammals. A "mammal" includes both human and non-human mammals, such as mice. The term "subject" further includes both human and animal subjects, such as dogs and cats, as well as other veterinary subjects. In some examples, a subject is a patient, such as a patient diagnosed with wound. In other examples, the subject is a veterinary patient, such a dog, cat, pig, or farm animal, for example, diagnosed with a wound.

As used herein, the terms "treating" or "treatment" includes prophylaxis of a disorder or condition, or alleviation of the symptoms associated with a disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

II. Description of Several Embodiments

Overview

The traditional method for placement of a tie-over bandage with the placement of traditional tie over loops requires a wide surgical prep. Typically a bite of the skin is taken and a suture is tied in one or more knots. A loop is formed from the remaining suture and tied with additional knots, so that the loop remains. A lacing material is then threaded through the loops and crisscrossed over a bandage to secure the bandage in place or place tension on the skin. Such a method is time consuming and requires significant skill to properly place and set the sutures. To solve these and other problems, the inventors have developed a device for securing an object to a subject and/or closing a wound in a subject, such as a wound in the skin or a subject.

Thus, disclosed is a device for securing an object to and/or closing a wound in a subject, such as an animal subjected, for example a veterinary or human subject. The disclosed device includes an anchor, a swivel connector and lacing loop. The anchor is mechanically connected to swivel connector, which is in turn mechanically connected to lacing loop. The anchor is configured to connect the device to a subject, for example through a bite of tissue, leaving the lacing loop free to be connected to a lacing material, much the same way the suture loop is constructed to allow the passage of a lacing material.

In some embodiments, the anchor of a disclosed device includes connector arc, an optional extension shaft, a needle shaft, a spring arc, a support shaft, a needle tip and a clasp. The support shaft connects spring arc, which is typically less than a full circle, to the connector arc, which is the portion of the anchor that mechanically connects the anchor to the swivel connector. The connector arc can also connect the support shaft to the optional extension shaft, which can act as the clasp or as a support for the clasp, as discussed later. The spring arc connects needle shaft, which terminates in a needle tip, to the support shaft. In some examples needle tip, needle shaft, spring arc support shaft, connector arc and, optionally, the extension shaft are a contiguous piece of material, such as a contiguous piece of wire.

In some embodiments, the disclosed device includes a protective plate, which may include clasp arm and/or stabilizing arm. In the closed position, the needle tip is secured with clasp, which may be attached to clasp arm of the protective plate, should the device be configured to include a clasp arm and/or a protective plate. In this embodiment of the device, the clasp helps keep the device secured to the subject or other materials, for example, and prevents accidental damage to tissues or other materials by guarding the needle tip of the needle shaft within the clasp. The clasp arm can also act as a guide for needle shaft, for example to help guild the needle shaft and optionally the needle tip into the clasp, for example ensuring that the needle shaft and thus the needle point are retained by the clasp. In some embodiments, the clasp arm also acts to protect the user and/or the subject from the needle tip, for example when the device is being deployed and/or retained in the tissue of the subject. In the closed position, needle shaft and in some examples the needle tip rests within the clasp keeping the needle shaft secured in place so that anchor remains attached to the subject or other material.

The spring arc, when in use, rests within the tissues or material to which it is attached. In some embodiments, the spring arc is flexible enough to allow needle shaft to move into the open position, but stiff enough to maintain its shape when in the closed position. Thus, spring arc is of sufficient stiffness, that when not engaged with the clasp, it holds needle shaft in the open position, for example allowing the user to easily guide the needle tip and needle shaft into the tissue of a subject. As needle shaft opens, the flexibility and elasticity of the spring arc allow it to adjust accordingly so that needle shaft remains in an open position. Typically, the spring arc is configured as a fraction of a circle although other configurations are conceivable. In some embodiments, the spring arc is a compound curve. In some embodiments, the spring arc and the needle shaft are an arc or form a compound curve. In some embodiments, the spring arc and the support shaft are an arc or form a compound curve. In some embodiments, the spring arc, the support shaft and the needle shaft are an arc or form a compound curve.

Positioning the anchor on a subject typically includes advancing the needle tip and needle shaft through a bite of the subject's tissue. For example, the needle tip and needle shaft are advanced through the bite of tissue such that spring arc is ultimately seated within the subject's tissue with the needle shaft and needle tip being outside the tissue to which the anchor is attached. After spring arc is seated, the needle shaft and/or the needle tip may be safely secured with the clasp.

The disclosed device further includes a swivel connector, which connects the anchor and the lacing loop. In certain embodiments, the swivel connector includes a barrel, a lacing loop fitting with a fenestration, such as a single fenestration, for attaching the lacing loop, and anchor fitting with anchor with a fenestration, such as a single fenestration, for attaching the anchor. The lacing fenestration and anchor fenestration are configured to allow attachment of the anchor and the lacing loop, respectively. In certain embodiments, the lacing loop fitting and anchor fitting may be configured as substantially cylindrical rods that can turn or rotate as described herein about an approximate horizontal plane within a support structure such as a barrel, for example a rotation about the major axis of barrel, and/or lacing loop fitting and/or anchor fitting. In such embodiments, lacing loop fitting and anchor fitting have portions within the support structure, such as a barrel that are configured so that they do not slip out of the ends of barrel. In certain embodiments, one or both of lacing loop fitting and the anchor fitting of the swivel connector are configured as a loop, for example as an eyehook loop.

In certain embodiments, the anchor fitting and/or lacing loop fitting includes a shaft extension which terminates in ball bearing or other shape, such as a flat nail head, that is of greater diameter than the shaft extension. Shaft extension and ball bearing lie within an internal space of the barrel of the swivel connector and allowed to rotate along a bearing race of the barrel of the swivel connector. Such a connection allows the anchor fitting and/or the lacing loop fitting to rotate freely with respect to the barrel, for example, clockwise or counterclockwise. The rotation conferred by the swivel permits the lacing loop and the anchor to lie in the same or different planes from each other so that excessive torque does not occur to the skin, tissues, materials, or lacing to which the device is attached or to which are attached to the device.

The device disclosed herein includes lacing loop, which is connected to the swivel connector, for example through the fenestration present in the lacing loop fitting of the swivel connector. In certain embodiments, the lacing loop includes a connecting loop, a threading loop and a threading arc. The connecting loop includes a connecting arc and the threading loop includes lacing arc. The lacing arc of the lacing loop connects connecting loop and threading loop and can provide the surface against which a lacing, cord, or other material may rest, for example when the device is deployed.

The lacing loop comprises any means through which may pass a cord, lacing, or other materials. For example, in certain embodiments, the lacing loop may be a simple ring or oval. In other embodiments, the loop may comprise a single, overlapping ring. In still other embodiments, the lacing loop may be a hook, for example, which is sufficient to retain a cord, lacing, or other lacing material used to secure a bandage, for example, or another device. In other embodiments, the loop may be a clasp, for example, that is capable of retaining a cord, lacing, or other material used to secure a bandage, for example, or another device. In other embodiments, the loop may be similar to the anchor, with a needle shaft that can be opened and closed, for example. In still other embodiments, the lacing loop may be a spiral, coil, hook, S-hook, or other shape that allows easy passage of lacing material, for example. In still other embodiments, the loops may be a snap, Velcro ring or strap, carabiner, or other device that can be easily opened and closed, for example. In other embodiments, the lacing loops could be a simple loop of elastic or inelastic, flexible or rigid material that, for example, can be laced by direct passage of lacing material or can be secured by a hook, knob, hanger, clasp, or other device or fastener. In one embodiment, the lacing loop can exist as two separate pieces of lacing material, strap, cord, or other material, for example, that can be tied or secured together with a fastener such as a clasp, crimp, spring-loaded clamp, Velcro, or other device, for example, to make a loop that surrounds the lacing material.

The devices of the present invention may be fabricated by a variety methods known to those skilled in the art, and they may comprise a variety of one or more materials such as metals, plastics, composites, or ceramics. For example, such materials include those commonly used in medical and surgical devices, such as steel, titanium, nickel, chromium, molybdenum, cobalt, combinations and alloys thereof, or other materials that are safe for use in or adjacent to live tissue.

The devices, methods, and systems disclosed herein are thus very advantageous for use in treating acute wounds, such as to control bleeding associated with traumatic injury. They can also be used independent of tissue thickness or type or presence of hair, oils, or moisture. The devices, methods, and systems are also advantageous because they may be used by those with minimal skill. In other words, unlike the traditional suture method, which takes significant practice and experience, one can use the devices, methods, and systems disclosed herein with minimal training or experience.

Exemplary Devices

FIG. 1 shows exemplary device 100 according to one embodiment for securing an object to, and/or closing a wound in, a subject, such as an animal subject, for example a veterinary or human subject. With reference to FIG. 1, device 100 includes anchor 120, swivel connector 140 and lacing loop 160. Anchor 120 is mechanically connected to swivel connector 140, which is in turn mechanically connected to lacing loop 160. Anchor 120 is configured to connect device 100 to a subject, for example through a bite of tissue such as the skin of the subject.

FIG. 2 shows anchor 120 of device 100 according to one example embodiment. Anchor 120 of device 100 includes connector arc 125, optional extension shaft 126, needle shaft 130, spring arc 132, support shaft 133, needle tip 135 and clasp 136. Support shaft 133 connects spring arc 132 to connector arc 125 of anchor 120. Connector arc 125 connects support shaft 133 to optional extension shaft 126. Spring arc 132 connects needle shaft 130 to support shaft 133. Needle tip 135 is the termination of needle shaft 130. Connector arc 125, optional extension shaft 126, needle shaft 130, spring arc 132, support shaft 133, needle tip 135 and clasp 136 can be formed from a single piece, such as a single piece of wire or from multiple pieces. Optionally, device 100 can include protective plate 137, which may include clasp arm 138 and/or stabilizing arm 139. In the closed position, as shown in FIG. 2, needle tip 135 is secured with clasp 136, which is attached to clasp arm 138 of protective plate 137. In this embodiment of device 100, clasp 136 helps keep device 100 secured to the subject or other materials, for example, and prevents accidental damage to tissues or other materials by guarding needle tip 135 of needle shaft 130 within clasp 136. Clasp arm 138 can also act as a guide for needle shaft 133, ensuring that needle shaft 133 and thus needle point 135 are retained by clasp 136. Clasp arm 138 also advantageously protects the user from needle tip 135. Protective plate 137 provides additional shielding of needle tip 135, for example. In the closed position, needle tip 135 rests within clasp 136 keeping the needle shaft 130 secured in place so that anchor 120 remains attached to the subject or other material, for example.

Needle shaft 130 can be manipulated to open or close anchor 120. In the closed position needle tip 135 rests under clasp 136, for example of protective plate 137. In the closed position, anchor 120 is secured by clasp 136 to the subject and has the advantage of preventing damage to tissues or other materials by guarding needle tip 135 of needle shaft 130.

In some example embodiments, anchor 120 comprises needle tip 135 that is sharpened to penetrate tissues, such as the tissues of a veterinary or human subject or other material. Needle shaft 130 penetrates through the tissues and/or other material during anchor placement, for example. As one skilled in the art will appreciate, a blunt ended needle shaft 130 may be may be adequate when anchor 120 is secured to tissue or material that is easy to penetrate, for example. Needle shaft 130 should be rigid enough to maintain its shape as it is pushed through tissue or other material. As one skilled in the art will appreciate, a more rigid needle shaft may be needed when anchor 120 is secured to non-tissue materials such as hard plastic, for example, whereas a less rigid shaft may be adequate when the anchor is secured to soft tissue such as the skin. In some embodiments, needle shaft 130 is substantially straight. In alternative embodiments, needle shaft 130 is slight curved, for example to aid in the placement of anchor 120 in the tissue of a subject, much the same way a suture needle is curved to aid in passing through the tissue of a subject. For example, needle shaft 130 can be straight, a segment of a circle, such as ¼ circle, ⅜ circle, ½ circle, ⅝ circle, a compound curve, a half curve (also known as ski), half curved at both ends of a straight segment (also known as canoe) or other or various radii. Needle point 135 of needle shaft 130 can be of various designs, such as pyramidal, taper (needle body is round and tapers smoothly to a point), cutting (needle body is triangular and has a sharpened cutting edge on the inside curve), reverse cutting (cutting edge on the outside), trocar point or tapercut (needle body is round and tapered, but ends in a small triangular cutting point), blunt points, side cutting or spatula points (flat on top and bottom with a cutting edge along the front to one side) or any variation.

Spring arc 132, when in use, rests within the tissues or material to which it is attached. One skilled in the art will appreciate that the needle shaft 130 and the spring arc 132 can be made of various sizes, such as lengths and thicknesses, depending on the use and the thickness of the tissue or material to which anchor 120 is secured. For example, inserting needle shaft 130 and spring arc 132 through the skin and also into deep tissue layers may at times be necessary, thus necessitating a longer needle shaft 130 and a longer and deeper spring arc 132. Alternatively, a more shallow anchor attachment may be sufficient in other applications, in which case embodiments of the devices with a shorter needle shaft 130 and shorter spring arc 132 may be more appropriate.

In some embodiments, spring arc 132 is flexible enough to allow needle shaft 130 to move into the open position, but stiff enough to maintain its shape when in the closed position. Thus, spring arc 132 is of sufficient stiffness, that when not engaged with clasp 136, it holds needle shaft 130 in the open position. Pressure can be applied to needle shaft 130, for example with fingers, forceps or other medical instruments, to overcome the resistance of spring arc 132 and lock anchor 120 closed by engaging needle shaft 130 and/or needle tip 135 with clasp 136. As needle shaft 130 opens, the flexibility and elasticity of spring arc 132 allow it adjust accordingly so that needle shaft 130 remains in an open position. Support shaft 133 helps stabilize anchor 120 and maintain its length. The length of the stabilizing shaft, in various embodiments, is made in various lengths depending on the thickness of the tissues or materials to which it will be attached. Support shaft 133 ends in connector arc 125 of anchor 120. In some embodiments, connector arc 123 has an extension shaft 126 that is encased in stabilizing arm 139 of protective plate 137. In some embodiments, extension shaft 126 forms clasp 136, in that they are a single piece of material. Connector arc 125 of anchor 120 permits attachment to the anchor fitting of the swivel connector 140, for example as discussed below. It is contemplated the spring arc can be a segment of a circle, such as ¼ circle, ⅜ circle, ½ circle, ⅝ circle, or even a compound curve In some example embodiments, anchor 120 includes protective plate 137, which in some embodiments includes clasp arm 138 and stabilizing arm 139, which aids in keeping anchor 120 in a specified shape and plane. Stabilizing arm 139, for example, aids in preventing independent movement of the extension shaft 126 of the connector arc 125 and the support shaft 133. It also provides in certain embodiments, clasp arm 138 with clasp 136 that can hold needle shaft 130 in a closed position to keep anchor 120 securely in place, thus preventing the needle tip 135 from damaging the tissues or other materials to which anchor 120 is connected. In some embodiments, stabilization between support shaft 130 and extension shaft 126 is made by twisting the two shafts around each other, for example twisting at least 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360° or more. In some example embodiments, stabilization between support shaft 130 and extension shaft 126 is made by pinching the two shafts together, for example, so that they touch or are close to touching. The two shafts can be mechanically attached, for example brazed, welded, or otherwise connected.

Positioning anchor 120 on a subject typically comprises advancing needle tip 135 and needle shaft 130 through a bite of the subject's tissue. For example, needle tip 135 and needle shaft 130 are advanced through the bite of tissue such that spring arc 132 is ultimately seated within the subject's tissue with needle shaft 130 and needle tip 135 being outside the tissue to which anchor 120 is attached. After spring arc 132 is seated, needle tip 135 may be safely secured with clasp 136.

In certain example embodiments, protective plate 137 may be fenestrated, for example leaving an opening between stabilizing arm 139 and clasp arm 138. In other embodiments, protective plate 137 may be solid for example as in the alternate embodiment of anchor 120 shown in FIG. 3A. One skilled in the art will appreciate other shapes and configurations of protective plate 137 that are operable and compatible in accordance with the devices, systems, and methods disclosed herein.

Figure 3A:
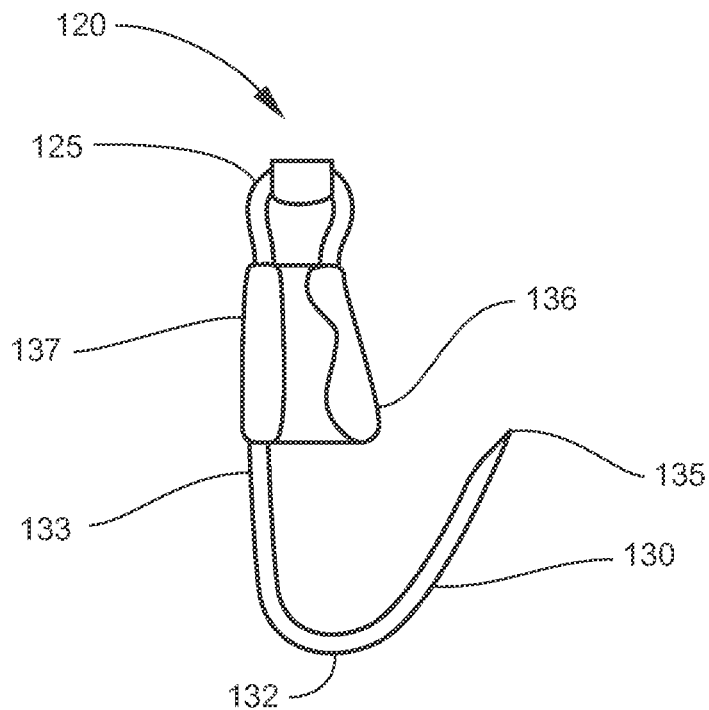
FIG. 3A is a front perspective view of an exemplary alternative embodiment of an anchor of the device for securing an object to a subject. The Anchor is shown in the open position.

With reference to FIG. 3A, which shows an alternate example embodiment of anchor 120, in the open position. As shown in FIG. 3A needle tip 135 of needle shaft 130 is free and can be easily inserted through tissues or other materials to secure the anchor in place to a subject or other material. In this embodiment protective plate 137 is solid, e.g. no fenestration and the clasp arm and stabilizing arm are integrated with clasp 136. Another alternate embodiment of anchor 120 is shown in FIG. 3B.

Figure 3B:
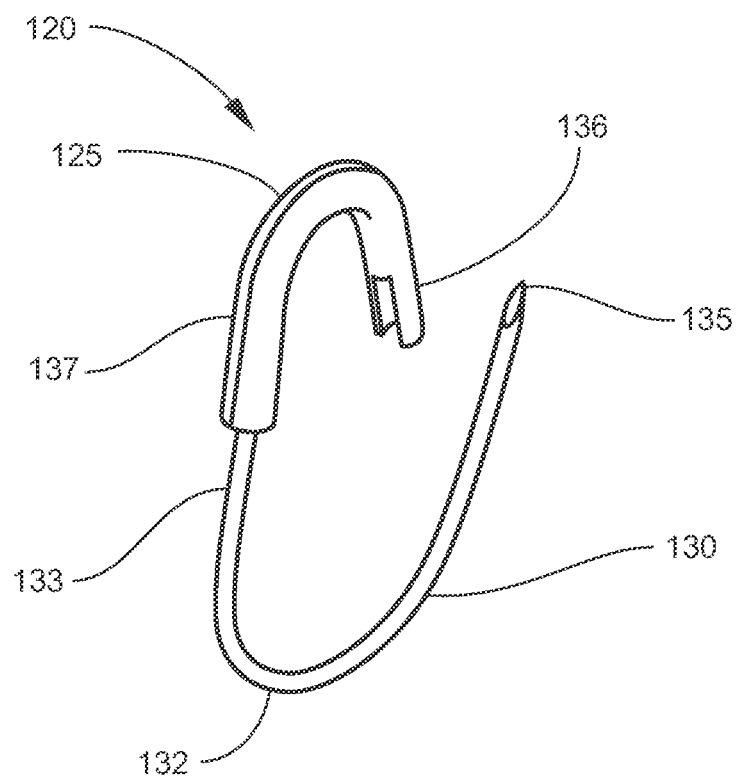
FIG. 3B is a perspective view of an exemplary alternative embodiment of an anchor of the device for securing an object to a subject. The anchor is shown in the open position.

With reference to FIG. 3B, which shows an alternate example embodiment of anchor 120, in the open position needle tip 135 of needle shaft 130 is free and can be easily inserted through tissues or other materials to secure anchor 129 in place to a subject or other material. In this embodiment, protective plate 137 forms connecting arc 125 and clasp 136. In such an embodiment, protective plate 137 may attach directly to stabilizing shaft 133, for example via a swage connection or other, or be configured to encircle connecting arc 125 and/or extension shaft 126.

Returning to FIG. 1, device 100 includes swivel connector 140, which connects anchor 120 and lacing loop 160. The details of an embodiment of swivel connector 140 are shown in FIG. 4. With reference to FIG. 4, in certain embodiments, swivel connector 140 includes barrel 145, lacing loop fitting 150 with lacing fenestration 151, and anchor fitting 155 with anchor fenestration 156. Lacing fenestration 151 and anchor fenestration 156 are configured to allow attachment of anchor 120 and lacing loop 160, respectively. In certain embodiments, lacing loop fitting 150 and anchor fitting 155 may comprise cylindrical rods that can turn or rotate as described herein about an approximate horizontal plane within a support structure such as a barrel 145, for example a rotation about the major axis of barrel 145, and/or lacing loop fitting 150 and anchor fitting 155. In such embodiments, lacing loop fitting 150 and anchor fitting 155 have portions within the barrel 145 are configured so that they do not slip out of the ends of barrel 145. For example, the portion of lacing loop fitting 150 and anchor fitting 155 within barrel may be larger than the hole of the barrel through which lacing loop fitting 150 or anchor fitting 155 extend. For example, during the manufacturing process, the ends of barrel 145 may be crimped or otherwise configured to encase a bulbous portion of lacing loop fitting 150 and/or anchor fitting 155 extend that is internal to barrel 145. Such a configuration thus keeps lacing loop fitting 150 and/or anchor fitting 155 from slipping out of barrel 145 but yet permit rotation as described herein. In some embodiments, a nut, washer, or thickening of lacing loop fitting 150 and/or anchor fitting 155 keeps lacing loop fitting 150 and/or anchor fitting 155 from slipping out of barrel 145.

Figure 5:
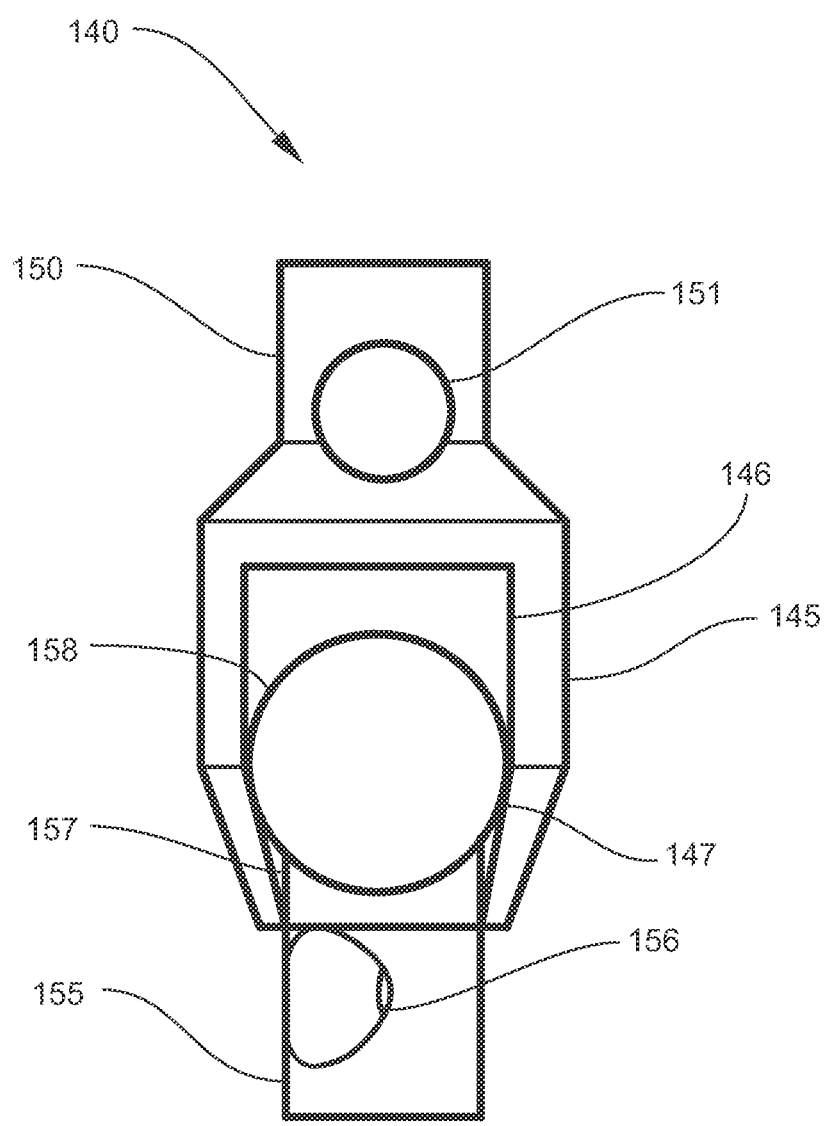
FIG. 5 is a cut away side perspective view of the exemplary embodiment of the swivel connector of FIG. 4. In this example embodiment, the swivel connector has one fixed fitting and one ball bearing fitting.

As shown in FIG. 5, in certain embodiments, anchor fitting 155 includes shaft extension 157 (which can be of greater, lesser or the same diameter as anchor fitting 155) which terminates in ball bearing 158, wherein ball bearing 158 is of greater diameter than shaft extension 157. Shaft extension 157 and ball bearing 158 lie within internal space 146 of barrel 145 of swivel connector 140 and rotate along bearing race 147 of swivel connector 140. Alternatively or additionally, in other embodiments, lacing loop fitting 150 may comprise a ball bearing (not shown), for example a shaft extension (which can be of greater, lesser or the same diameter as anchor fitting 155) that terminates in ball bearing of greater diameter than the extension shaft. In other embodiments, both anchor fitting 155 and lacing loop fitting 150 comprise extension shafts terminating in a ball bearing. Such a connection allows anchor fitting 155 and/or lacing loop fitting 150 to rotate freely with respect to barrel 145, for example, clockwise or counterclockwise as described herein. For example, such as connection may allow anchor fitting 155 and/or lacing loop fitting 150 to rotate freely with respect to barrel 145 with a rotation of about 0°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360° or more. The rotation conferred by the swivel permits the lacing loop 160 and the anchor 120 to lie in the same or different planes from each other so that excessive torque does not occur to the skin, tissues, materials, or lacing to which the device is attached or to which are attached to the device. In some embodiments, anchor fitting 155 or lacing loop fitting 150, but not both, is connected to barrel 145 such that either anchor fitting 155 or lacing loop fitting 150 does not rotate with respect to barrel 145, while the other does. In certain embodiments, lacing loop fitting 150 is an extension of barrel 145. In other embodiments, lacing loop fitting 150 ends in a ball bearing that resides within the barrel 145. In certain embodiments, anchor loop fitting 155 is an extension of barrel 145. In other embodiments, anchor loop fitting 155 ends in a ball bearing that resides within the barrel 145. In certain embodiments, the swivel connector is rigidly connected to the lacing loop and/or the anchor. For example, with reference to FIG. 2 lacing loop 150 can be rigidly connected to swivel connector 140, such as barrel 145, or loop fitting 150. Additionally or alternatively, anchor 120 can be rigidly connected to swivel connector 140, such as rigidly connected to barrel 145, or anchor fitting 155.

In certain embodiments, connector arc 125 of anchor 120 slides back and forth through anchor fenestration 156 of the swivel connector 140 or rocks back and forth within fenestration 156 to allow motion, thus reducing the torque on the skin, tissue, or material through which anchor 120 is passed. Unlike the traditional method for placement of a tie-over bandage, the devices disclosed herein can be used rapidly. For example, the time required to place a tie-over bandage on a subject as compared to the traditional suturing methods may be reduced by at least about 10%, 20%, 30%, 40%, 50%, 60%, 70%, 80%, or 90% (or values in between) depending on the size of the wound and the number of devices needed.

Returning to FIG. 1, device 100 includes swivel connector 140, which connects anchor 120 to the lacing loop 160. With reface to FIGS. 1-4, in some embodiments, anchor fitting 155 contains an anchor fenestration 156, through which passes the connector arc 125 of the anchor 120. In some embodiments, lacing loop fitting 150 contains a lacing loop fenestration 151, through which passes a portion of the lacing loop, described below.

Figure 6:
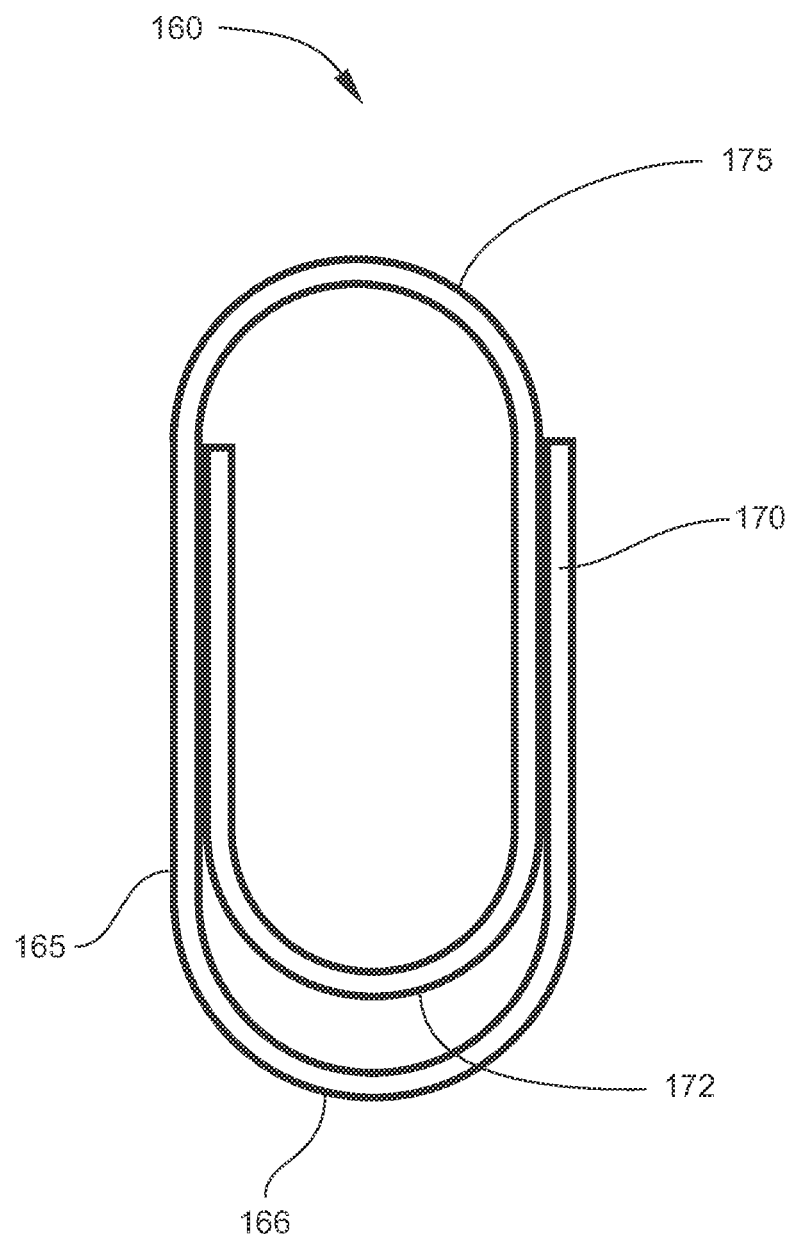
FIG. 6 shows a front perspective view of an exemplary embodiment of a lacing loop of the device for securing an object to a subject.

As shown in FIG. 1, device 100 includes lacing loop 160 that is connected to swivel connector 140. The details of an embodiment of lacing loop 160 are shown in FIG. 6. With reference to FIG. 6, in certain embodiments, lacing loop 160 includes connecting loop 165, threading loop 170 and threading arc 175. Connecting loop 165 includes connecting arc 166. Threading loop 165 includes lacing arc 171. With reference to FIGS. 4 and 6, connecting arc 166 of connecting loop 165 is fitted through lacing fenestration 151 of lacing loop fitting 150 of swivel connector 140, (see e.g. FIG. 1) within which connecting arc 166 rests, rocks, or slide. Such a configuration allows the lacing loop 160 to slide within fenestration 151 of lacing loop fitting 150 and provides the ability to place lacing loop 160 in a variety of positions, for example with respect to the tissue of a subject. It further allows lacing loop 160 to shift as tension is placed on lacing loop 160, for example tension applied by lacing, cord, or other material. Lacing arc 175 of lacing loop 160 connects connecting loop 165 and threading loop 170. Lacing arc 175 for example, provides the surface against which the lacing, cord, or other material may rest. In some embodiments, connecting loop 165 and threading loop 170 are not in the same plane, such that the loops are not in contact, for example threading loop 170 can be slightly elevated relative connecting loop 165. Such placement of connecting loop 165 and threading loop 170 allows the lacing material to be passed under threading loop 170 to fall within and across the lacing arc 175 and within the space of threading loop 170. The slight elevation is advantageous because the lacing material, for example, can be passed swiftly or easily under the threading loop without having to thread the lacing end through the loop. The avoids the difficulty encountered, for example, when attempting to thread the free end of lacing material through the lacing loop in an awake subject that is moving because of stress, anxiety, or excitement.

Figure 7:
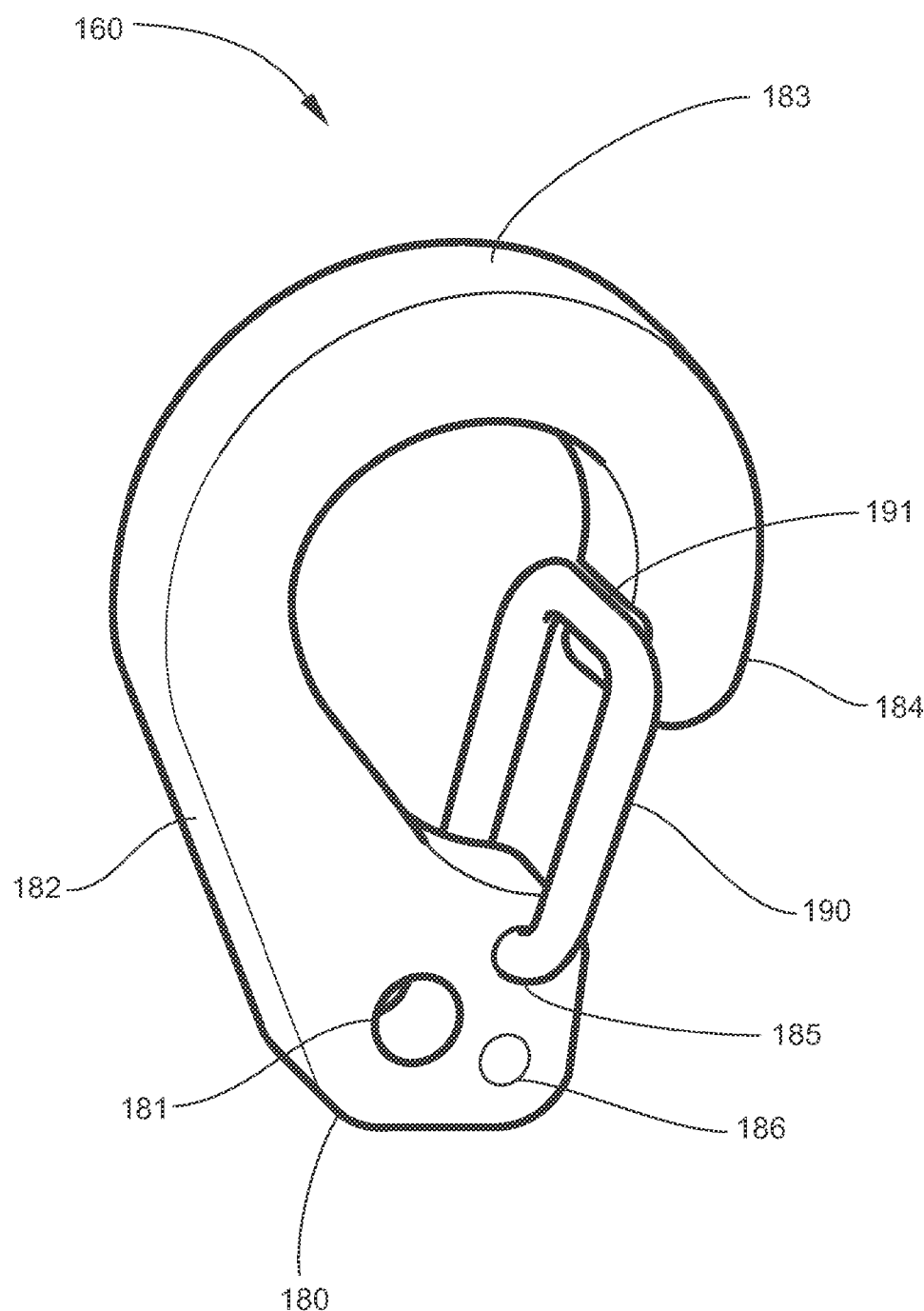
FIG. 7 shows an oblique perspective view of an exemplary embodiment of a lacing loop of the device for securing an object to a subject.

With reference to FIG. 7, which shows an exemplary alternate embodiment of lacing loop 160, the lacing loop may be shaped like a hook, with its opening covered by a spring wire. In embodiments, the spring wire is configured, such as bent, folded, looped, or arced in approximately its central third to make a tongue-like projection. The two ends of the spring wire are secured to the base, stem, or neck of the lacing hook, and the apex of the wire projection formed by the central bend, fold, loop, or arc extends away from the base, stem, or neck of the lacing hook. The two ends of the spring wire are secured to the base, stem, or neck of the lacing hook, and the apex of the wire projection formed by the central bend, fold, loop, or arc extends away from the base, stem, or neck of the lacing hook. The spring wire can easily be pushed inwards during insertion of the lacing material. Because the apex of the spring wire overlaps the inner arc of the hook, the spring wire prevents the lacing material from inadvertently exiting the lacing hook. Use of this lacking hook permits rapid placement and secure retention of the lacing material. With reference to FIG. 7, in certain embodiments, lacing loop 160 includes hook base 180, which is configured to connect to the swivel connector through hook base fenestration 181, hook arm 182, threading hook 183 and hook tip 184. Hook base 180 further includes fenestrations 185 and 186, which are configured to fit the ends of spring wire 190. In the embodiment shown in FIG. 7, fenestrations 185 and 186 are offset which results in tension being exerted on spring wire 190 to hold spring wire 190 in the closed position, as shown, with spring wise tip 191 against hook tip 184.

With reference to FIG. 1, swivel connector 140 allows anchor 120 and lacing loop 160 to swivel or rotate about each other in at least an approximate horizontal plane. Although such rotation is not required, the rotation further reduces the torque on skin or other materials to which the anchor may be attached. This prevents unnecessary damage to the skin, for example, and is more comfortable for the subject. This in turn promotes patient compliance, for example. Swivel connector 140 permits clockwise or counter clockwise rotation (or both) from about 0° to up to and beyond 360°, e.g., swivel connector 140 in certain example embodiments permits free rotation in either a clockwise or counterclockwise direction (or both) about a horizontal plane. For example, the swivel may permit rotation of about 0°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360° or more.

In some example embodiments, connector arc 125 of anchor 120 may be used as a site for direct passage of lacing material such as in the space between connector arc 125 and protective plate 137 or it may be left empty. In certain other example embodiments, a lacing loop, for example, may be directly connected to connector arc 125 such that lacing material may pass through the lacing loop. In other words, a swivel may not be necessary in some embodiments. In such embodiments, connector arc 125 may slide in a variety of directions, thus allowing a wide range of motion. This advantageously prevents torque and pulling of the tissue or material to which the anchor 120 is attached.

The devices of the present invention may be fabricated by a variety methods known to those skilled in the art, and they may comprise a variety of one or more materials such as metals, plastics, composites, or ceramics. For example, such materials include those commonly used in medical and surgical devices, such as steel, titanium, nickel, chromium, molybdenum, cobalt, combinations and alloys thereof, or other materials that are safe for use in or adjacent to live tissue. In certain example embodiments, the devices disclosed herein are made of surgical steel. In some example embodiments, only anchor 120, for example, is made of surgical steel. In still other example embodiments, only the needle tip 135, needle shaft 130, arc spring 132, and support shaft 133 are made of surgical steel. In some example embodiments, the device comprises only the anchor or anchor and swivel. Further, the devices disclosed herein may be adapted to many sizes depending on their intended use. For example, device 100 comprising anchor 120, swivel connector 140, and lacing loop 160 may be manufactured to various sizes and specifications as those skilled in the art will appreciate.

Exemplary Methods

Several uses are contemplated for the various devices and embodiments thereof disclosed herein. In one exemplary embodiment, a system is provided for attaching an object to a subject, comprising one or more of the devices disclosed herein; and, a lacing material, wherein the lacing material is threaded through the one or more lacing loops of the two or more devices. The length of the lacing material, for example, may be a predetermined length, and may comprise single or multiple pieces of lacing material. For example, the length of the lacing material may be determined based on the number of devices that are being connected, with more devices necessitating a longer length of lacing material. Wound size may also dictate the length of the lacing material, with larger wounds necessitating longer lacing material, for example. For example, single or multiple pieces of the lacing material may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 inches long. After the lacing material is threaded through the lacing loops, excess material may be removed, for example, by cutting the material.

Figure 8A:
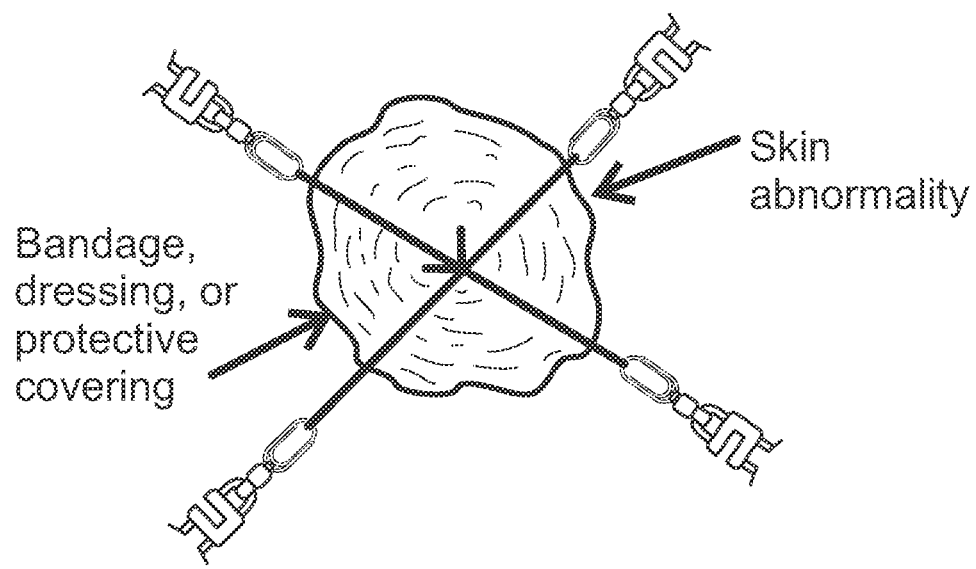
FIG. 8A is an illustration showing the use of multiple devices to secure a bandage over the skin.

In some example embodiments, the devices disclosed herein may be used to apply tension and compression to a bandage covering wound. As shown in FIG. 8A, for example, the devices, methods, and systems disclosed herein may be used to increase tension on or around tissue such as the skin or, when necessary, to stretch the tissue. An anchor 1 is inserted in the skin, for example. The lacing material is passed through the lacing loop of one device and across a wound, bandage, or other material to the opposite device. Another piece of lacing material is passed through additional devices that are opposite to each other. The lacing material is tightened to place tension on the skin, which in turn stretches the skin and reduces tension on the wound or incision. It also increases compression on the bandage.

To increase tension and compression further in such embodiments, lacing material that is stretchable may be used. Such embodiments are advantageous, for example, because the devices, methods, and systems can withstand greater force than traditional suture loops. In other words, the lacing material can be pulled tighter than with traditional sutures because there are no sutures that come apart or stretch. And unlike traditional suture loops which resist later tightening of the lacing material because of friction between the lacing material and suture material, the devices, methods, and systems disclosed herein provide smooth surfaces so that such tightening or readjustment of the lacing material can readily be accomplished.

Figure 8B:
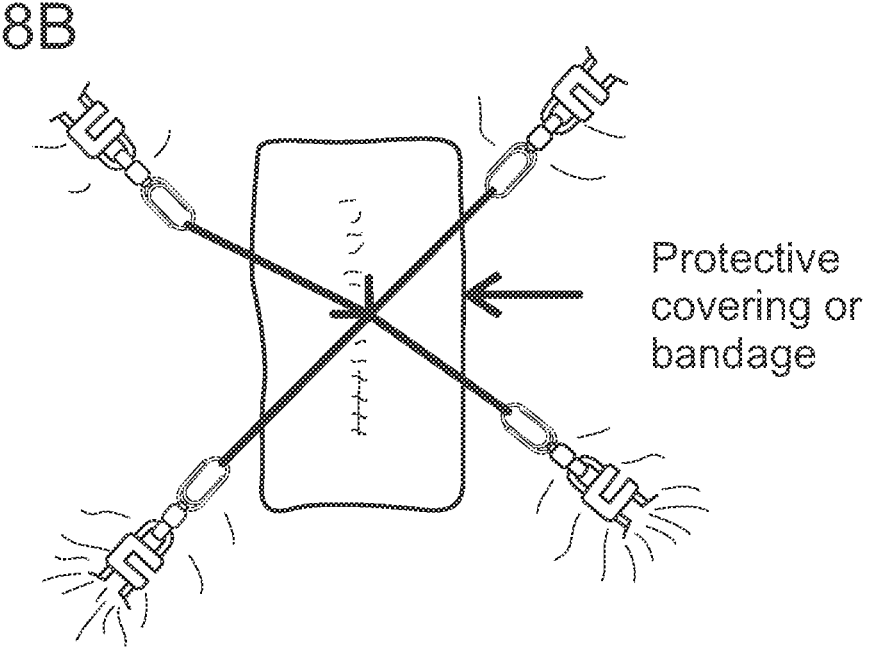
FIG. 8B is an illustration showing the use of multiple devices to secure a bandage over the skin.

In some example embodiments, such as those disclosed in FIG. 8B, for example, pressure may be applied to an acute wound to both hold the bandage in place and to stop bleeding. Further, if the wound is in a location where tension commonly exists on the wound, such as an incision on or across a knee or an elbow, the devices, methods, and systems disclosed herein may be advantageously used to shift the tension to another part of the body and away from the wound. This is in turn promotes healing of the wound as the tension that normally arises around the wound, and that often separates the wound, is alleviated.

In other example embodiments, tension can be applied to recruit tissue such as skin before or after a surgical procedure. For example, before the surgical removal of a tumor, skin may be recruited so that, after the tumor is removed, the excess skin can be used to close the surgical wound caused by removal of the tumor. Using the devices, methods, and systems disclosed herein, up to about 5%, 10%, 15%, 20%, 25%, 30%, 35%, or 40% more tissue such as skin may be recruited. Such embodiments may also be used to recruit tissue after the removal of a tumor, for example, or after a wound in which patches of skin have been removed or in which the wound is otherwise unstable and susceptible to breakdown from tension on the wound. To recruit such tissue, the lacing material may also be periodically tightened. For example, tightening and adjustment of the lacing material about every 2, 4, 6, 8, 10, 12, 14, 16, 18, 20, 22, 24, or 48 hours to as described herein may be needed. In other example embodiments, the lacing material can be attached to a device that provides gradual or continuous tightening until such time as the desired tension or skin recruitment is reached or the device is turned off, disengaged, or removed, for example.

Figure 8C:
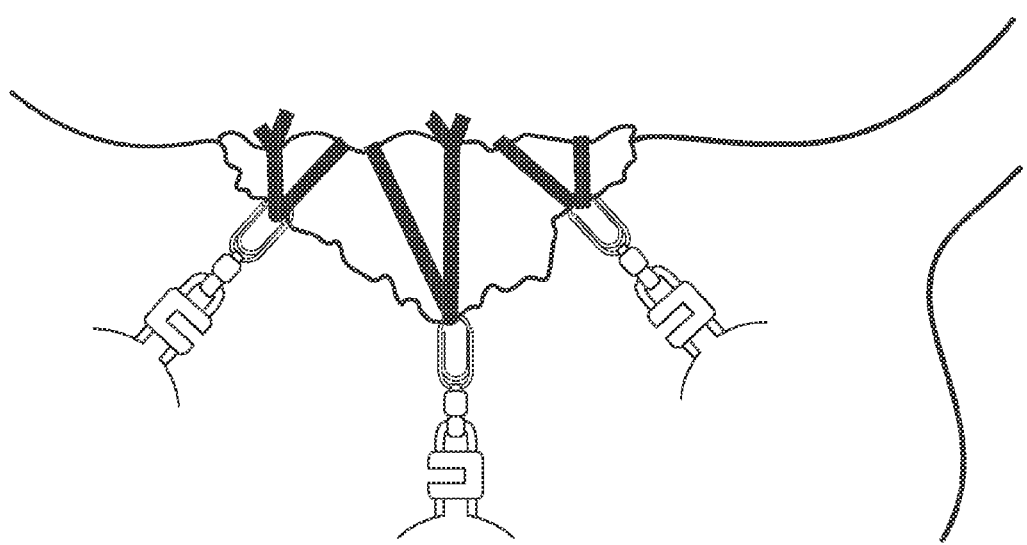
FIG. 8C is an illustration showing the use of multiple devices to secure a bandage over an irregular surface.

In some example embodiments, multiple devices are placed around a wound and object such as a bandage as shown in FIG. 8C. As shown, the devices, methods, and systems disclosed herein may be used to focally place bandages over difficult or uneven areas of a subject such as across the back of a dog. With tightening of the lacing material 26, pressure, forces, such as compression over the wound, can be applied to hold the bandage in place, for example, on such areas of the subject. This allows the subject greater flexibility and motion around the wound site than would otherwise be associated with traditional suture loops as such loops do not allow as much flexibility as the devices disclosed herein or may distort, stretch, or break under tension, for example. As shown, a bandage, packing, dressing, or other material is placed over the wound, for example. The lacing material is crisscrossed across the wound and threaded through the lacing loop of the device through the opening of the connector arc of the anchor when the anchor is used as the sole device.

Figure 8D:
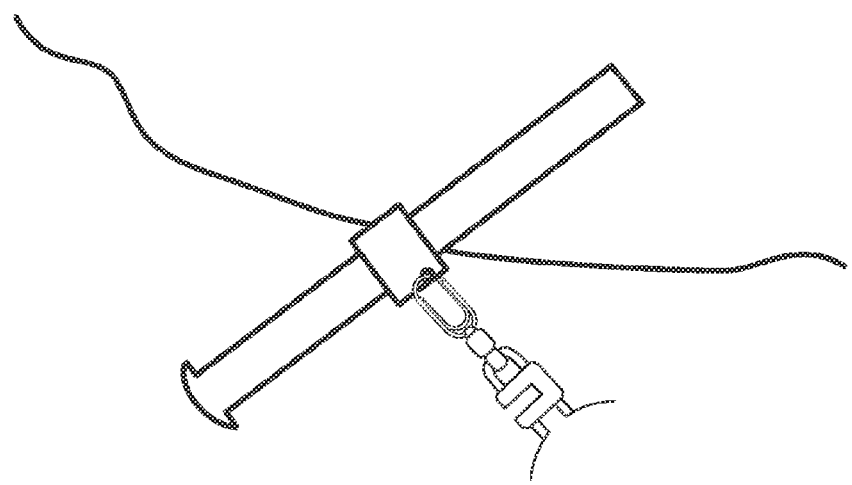
FIG. 8D is an illustration showing the device used to secure a tube, catheter, or other structure or device to a subject or other material.

In other example embodiments, such as is shown in FIG. 8D, the device can be used to attach or position one or more objects to a subject such as to the tissue of the subject or to a bandage or material, such as a strap, collar, bracelet, halter, adhesive, tag, protective clothing, splint, cast, or other device, object, or material, for example, secured to a subject so as to secure the object in place or position the object in place on the subject. For example, the device may be secured to an object directly or, in other embodiments, the device may be secured to a fastener that is attached to the object. Traditionally, feeding tubes, for example, may be secured to a subject with tape that is sutured to the subject. To reposition the tube, the sutured tape must traditionally be removed and then new tape and sutures introduced. The devices, methods, and systems disclosed herein address this painful and difficult procedure by providing a means for easily and rapidly readjusting objects that are secured to the subject. As described herein, the anchor can easily and quickly be repositioned, as there is no need for sutures.

In some example embodiments, the anchor may be used alone, i.e., without requiring a swivel or lacing loop, to hold skin, fascia, or other tissues together. The anchor or combination of anchors can be used in place of sutures, staples, or other tissue fasteners known in the art, for example, to facilitate skin apposition and wound closure. Such embodiments, for example, permit rapid and simplified closure of tissue wounds, and thus provide a means for rapid and efficient closure wounds including traumatic wounds, for example. They also allow for temporary closer of a wound. In some embodiments, the devices disclosed herein comprise only the anchor and swivel. For example, lacing material may be attached directly to the swivel. In some embodiments, the devices disclosed herein comprise only the anchor. For example, lacing material may be attached directly to the anchor.

In other example embodiments, the devices, methods, and systems disclosed herein may be used for body cavity care. For example, in the case of a severe infection, such as an infection of the abdomen, the infection must be drained. Traditionally, a zipper may be sewn into the subject so that the cavity can be repeatedly and intermittently opened to drain the infection. A severe infection of abdomen, for example, may be accessed, opened, and drained using the devices, methods, and systems disclosed herein without the need for sewing a zipper into the subject. In other embodiments, tension can be placed on the anchors secured in the abdominal wall fascia or muscle to stretch the fascia or muscle, for example. This will advantageously allow closure of the abdominal cavity in patients in which closure without pretensioning or stretching is not possible, as with a hernia or compartment syndrome, for example.

In some example embodiments devices, methods, and systems disclosed herein may be used to reduce motion of a body part. For example, an animal's tail may be immobilized as shown by attaching a first device to the subject, attaching a second device to the subject, and then connecting the first and second devices. In some embodiments, the first or second device may be attached to material other than the subject's tissue such as tape, for example. In other embodiments, the devices disclosed herein may be used to connect and object to another object, such as one bandage to another bandage.

In some example embodiments, for example, the disclosure provides a variety of methods that can be used to adjustably secure the devices to each other, to other devices, or to other objects. The loose ends of the lacing material may be secured together and adjusted to apply tension to the lacing material, thus applying pressure to any underlying object so that the object is secured in place, for example.

In some example embodiments, the lacing material further comprises a means for adjusting the length of the lacing material so that objects can quickly and easily be attached to the subject and pressure applied. For example, the lacing material is held together by a buckle or sliding mechanism. The lacing material is secured to itself with a hook, knob, or projection that is secured to a loop, eye, grommet, or other opening or fastener. Such embodiments are particularly advantageous for very rapid attachment of an object to a subject. In some embodiments, the lacing material is held together by a self retaining spring loaded device, for example. In some embodiments, the lacing material is held together by a clasp, clamp, clip, or similar fastener. In some example embodiments, the lacing loops are held together by a hook, clasp, snap, carabiner, or fastener. Alternatively, in other embodiments the lacing loops are hooked directly to each other. The exemplary design of these lacing methods allows tension to be adjusted or the lacing to be secured or unsecured rapidly or easily.

In another example embodiment, the anchor may be used to secure an identification tag to an animal. For example, the needle tip of the anchor may be passed through the ear of the animal, after which the device may be closed with the needle tip being placed behind a clasp. Such embodiments are advantageous because they allow for easy and rapid tagging of animals, inasmuch as they do not require additional machinery or other implements, for example, to attach the device and accompanying tag.

EXAMPLES

Using the traditional suture method to attach and secure a tie-over bandage, four suture loops were affixed to a piece of foam intended to replicate the skin of a subject. Briefly, the suture loops were placed at the four corners of a rectangular surface area roughly six inches by four inches. A roughly 4×6 gauze bandage was then aligned over the rectangular area. Cloth lacing material was then threaded through the four loops of the suture loops in crisscross pattern. The lacing material was then tightened and secured. The total time to secure the bandage to the simulated skin was 3 min and 44 seconds (i.e., 224 seconds).

The above experiment was repeated a second time, except that four prototype devices were used as described herein to replace the traditional suture loops. Briefly, four devices were placed at the four corners of a rectangular surface area roughly six inches by four inches in accordance with the methods described herein. A roughly 4×6 gauze bandage was then aligned over the rectangular area. Cloth lacing material was then threaded lacing loops of the device in crisscross pattern. The total time to secure the bandage to the simulated skin was 1 min and 10 seconds (i.e., 70 seconds). Hence, use of the prototype devices decreased the time to secure the bandage by about 71% as compared to the traditional method.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for securing an object to soft tissue of a subject, comprising:
   providing an anchoring device comprising:
     an anchor configured to couple to the soft tissue of the subject;
     a swivel connector having a proximal end and a distal end, the distal end of the swivel connector being coupled to a proximal end of the anchor;
     a lacing loop coupled to the proximal end of the swivel connector, and providing a lacing material threadable through the lacing loop;
   attaching the anchor to the soft tissue of the subject;
   threading the lacing material through the lacing loop; and,
   affixing the object to the subject with the lacing material.

2. The method of claim 1, wherein the swivel connector allows the lacing loop to rotate relative to the anchor.

3. The method of claim 1, wherein the anchor comprises:
   an elongate needle shaft having a distal end and a proximal end;
   a sharpened needle tip positioned on a distal end of the needle shaft and configured to pierce the soft tissue;
   a spring arc positioned on the proximal end of the needle shaft, wherein the spring arc is configured to rest within the soft tissue;
   a connector arc configured to permit attachment of the anchor to the swivel connector;
   an elongate support shaft positioned between the spring arc and the connector arc, wherein the support shaft has a shaft length; and
   a clasp positioned adjacent the needle tip and configured to prevent the needle tip from accidentally damaging the soft tissue.

4. The method of claim 3, wherein the anchor further comprises an extension shaft, and wherein the clasp is integrated into the extension shaft.

5. The method of claim 4, wherein the anchor further comprises a protective plate.

6. The method of claim 5, wherein the clasp is integrated into the protective plate.

7. The method of claim 5, wherein the connector arc is integrated into the protective plate.

8. The method of claim 5, wherein the protective plate comprises a stabilizing arm.

9. The method of claim 5, wherein the protective plate comprises a clasp arm.

10. The method of claim 3, wherein attaching the anchor to the soft tissue of the subject comprises advancing the needle tip and at least a portion of the needle shaft through a bite of the soft tissue of the subject until the spring arc is seated within the soft tissue and the needle tip is positioned outside the tissue to which the anchor is attached.

11. The method of claim 10, further comprising securing the needle tip with the clasp after the spring arc is seated.

12. The method of claim 1, wherein the swivel connector comprises a barrel, a fenestrated lacing loop fitting and fenestrated anchor fitting.

13. The method of claim 12, wherein at least one of the fenestrated lacing loop fitting and the fenestrated anchor fitting is a contiguous extension of the barrel.

14. The method of claim 12, wherein at least one of the fenestrated lacing loop fitting and the fenestrated anchor fitting is configured to freely rotate with respect to the barrel.

15. The method of claim 12, wherein at least one of the fenestrated lacing loop fitting and the fenestrated anchor fitting includes an extension shaft that terminates in a ball bearing that resides within a space within the barrel, and wherein the barrel is configured to retain the ball bearing.

16. The method of claim 15, wherein the ball bearing is of greater diameter than the shaft extension.

17. The method of claim 12, wherein the anchor is mechanically coupled to the swivel connector through the fenestrated anchor fitting, and wherein the lacing loop is mechanically coupled to the swivel connector through the fenestrated lacing loop fitting.

18. The method of claim 1, wherein the lacing loop comprises a connecting loop, a threading loop, and a threading arc.

19. The method of claim 1, wherein the connecting loop and the threading loop are not in the same plane such that connecting loop and the threading loop are not in contact.

20. The method of claim 1, wherein the lacing material comprises a hook that is attached to at least one end of the lacing material.

* * * * *